United States Patent [19]

Ebara

[11] Patent Number: 5,246,434
[45] Date of Patent: Sep. 21, 1993

[54] BLOOD COLLECTING TUBE
[75] Inventor: Yukinori Ebara, Suita, Japan
[73] Assignee: Nissho Corporation, Osaka, Japan
[21] Appl. No.: 873,108
[22] Filed: Apr. 24, 1992

[30] Foreign Application Priority Data

Apr. 26, 1991 [JP] Japan .................................. 3-125483
Oct. 31, 1991 [JP] Japan .................................. 3-314041

[51] Int. Cl.[5] ............................................. A61B 5/14
[52] U.S. Cl. ..................................... 604/403; 128/760
[58] Field of Search ...................... 604/403, 415, , 411;
215/247, 248, 249; 128/760, 763, 764

[56] References Cited

U.S. PATENT DOCUMENTS

| | | | |
|---|---|---|---|
| 1,941,071 | 12/1933 | Baxter | 604/403 X |
| 2,314,167 | 3/1943 | Shaw | 604/403 |
| 3,734,080 | 5/1973 | Petterson et al. | |
| 3,890,955 | 6/1975 | Elliott | |
| 3,900,028 | 8/1975 | McPhee | 604/415 |
| 4,312,349 | 1/1982 | Cohen | 604/415 X |
| 4,465,200 | 8/1984 | Percarpio | 604/415 X |
| 4,501,781 | 2/1985 | Kushida et al. | |
| 4,643,199 | 2/1987 | Jennings, Jr. et al. | |
| 4,863,453 | 9/1989 | Berger et al. | 604/415 |
| 4,967,919 | 11/1990 | Earhart | |
| 4,985,026 | 1/1991 | Kasai et al. | 604/403 |
| 5,061,263 | 10/1991 | Yamazaki et al. | 604/415 X |
| 5,084,040 | 1/1992 | Sutter | 604/415 X |
| 5,125,921 | 6/1992 | Duschek | 604/415 |

FOREIGN PATENT DOCUMENTS

| | | | |
|---|---|---|---|
| 221719 | 6/1962 | Austria | 604/415 |
| 524169 | 4/1956 | Canada | 604/415 |
| 348762 | 1/1990 | European Pat. Off. | |
| 1269805 | 7/1961 | France | 604/415 |
| 1388451 | 6/1965 | France | |
| 2-49099 | 2/1990 | Japan | |

OTHER PUBLICATIONS

Abstract: J53026877.

*Primary Examiner*—Danton D. DeMille
*Assistant Examiner*—Sam Rimell
*Attorney, Agent, or Firm*—Birch, Stewart, Kolasch & Birch

[57] ABSTRACT

A blood collecting tube includes a bottom-closed tubular member closed at one end and open at the other end, a stopper having an upper flange portion and a lower annular skirt portion extending therefrom and fitted in the open end of the tubular member, and a cap member placed on the tubular member. The tubular member has an annular flange so designed that its diameter increases in the direction toward the closed bottom to form a groove between its flange and the flange of the stopper whereas the cap member is provided with at least two inward projections of which one projection is adapted to engage with the flange of the tubular member, the other projection being engaged with the flange of the stopper and held in the groove.

11 Claims, 2 Drawing Sheets

BLOOD COLLECTING TUBE

BACKGROUND OF THE INVENTION

1. Field of the Invention

The present invention relates to a blood collecting tube and, more particularly, an evacuated blood collecting tube with an improved sealing assembly capable of being easily fitted to a bottom-closed tubular member and having a low resistance to insertion and removal of a piercing needle for collection of a blood sample.

2. Description of Related Art

In the medical field, evacuated blood collecting tubes are widely used to collect blood samples from patients. The blood collecting tube generally comprises a bottom-closed tubular member, i.e., a tubular member closed at one end and open at the other end, which is evacuated and sealed by a stopper fitted in the open end of the tubular member to retain its vacuum. Such tubular members are made of glass at the beginning, but the most of recent tubular members are made of synthetic resins as the glass tubes are easy to break and cause the problem of waste disposal. Such blood collecting tubes are disclosed, for example, in U.S. Pat. Nos. 3,734,080 and 3,890,955, and Japanese patent publication No. Heisei 2-49099.

The blood collecting tubes widely used include a bottom-closed tubular member made of synthetic resins having a small gas-permeability or a good gas-barrier property, such as polyethylene terephthalate for example, the tubular member being evacuated and closed by fitting a stopper made of elastomeric material such as butyl rubber or natural rubber in the open end of the tubular member under a reduced pressure. However, such blood collecting tubes have such a disadvantage that the quality deteriorates gradually during storage as gases such as air diffuses through the tubular member and stopper and causes lowering of the degree of vacuum in the evacuated tube. Thus, there is an increasing demand for evacuated blood collecting tubes with good quality.

Further, the above blood collecting tubes include the following problems as the stopper is held in place by frictional resistance between an annular outer surface of the stopper and an annular inner surface of the evacuated tube. For example, when collecting blood samples from a patient, it is common practice to use the evacuated blood collecting tube in combination with a holder having a double ended cannula of which one end is adapted to be pierced into a blood vessel while the other end is adapted to be penetrated into the stopper. In this case, blood samples are collected by first piercing one end of the cannula of the holder into a blood vessel of the patient, inserting the other end of the cannula into the tube through a diaphragm portion of the stopper, removing the cannula from the blood vessel, and then removing the holder from the blood collecting tube containing a collected blood sample.

Since the stopper possesses a large resistance to insertion of cannula, it is required to use a large-sized cannula to prevent it from bending during insertion of the cannula into the stopper. The greater the diameter of cannula, the greater the resistance to insertion and removal of the cannula. Thus, there is fear that the stopper may slip out of the tube at the time of removal of the holder if the frictional resistance between the stopper and cannula is greater than the frictional resistance between the tubular member and stopper. Further, the use of a large-sized cannula would load the patient at the time of collection of blood samples.

In addition, the rubber stopper removed from the tubular member is occasionally reused to close the open end of the tubular member. In this case, the insertion of the stopper causes compression of air in the bottom-closed tubular member, which causes a phenomenon that the stopper hops up.

On the other hand, if the above blood collecting tubes are used to supply the blood samples to an automatic blood analyzer having a hollow needle for taking blood samples from the tube, the rubber stopper occasionally comes off as the frictional resistance between the stopper and the needle pierced therein exceeds the frictional resistance between the tubular member and the stopper, resulting in leakage of the blood sample in the analyzer.

Japanese patent publication No. Heisei 2-25611 (corresponding to U.S. Pat. No. 4,465,200) discloses a blood collecting tube with an improved closure assembly comprising an annular stopper body with an upper outwardly extending annular flange portion and a lower annular skirt portion, and a flexible cap body for mounting on the annular stopper body. This closure assembly makes it possible to reduce the incidence of contamination of the user of the evacuated tube, but it includes problems similar to those disclosed in the aforesaid U.S. patents.

Japanese patent unexamined publication No. Heisei 2-212768 discloses a blood collecting tube of a thin film type composed of a tubular member closed at one end and open at the other end, a cap member removably fitted on the open end of the tubular member with a threaded structure, and a sealing member arranged between the cap member and the open end of the tubular member to seal the opening of the tubular member, said sealing member having a gas barrier film such as an aluminum laminated film and a re-sealing member made of natural rubber and bonded to the gas barrier film member in an overlapped relation. The blood collecting tube of the kind has various advantages, but it is impossible to remove the sealing member and cap member with one hand as the cap is screw-mounted on the tubular member.

SUMMARY OF THE INVENTION

It is therefore a general object of the present invention to provide a blood collecting tube with an improved sealing structure which makes it possible to reduce the resistance to insertion and removal of a hollow needle, as well as to prevent a stopper from slipping out of place when removing a hollow needle pierced into the stopper.

A further object of the present invention is to provide an evacuated blood collecting tube which can be used for analysis of blood samples with an automatic blood analyzer, without causing leakage of the blood sample into the analyzer.

Another object of the present invention is to provide an evacuated blood collecting tube which can be manufactured in the same manner as that of the evacuated blood collecting tubes of glass.

The above objects of the present invention are achieved by providing a blood collecting tube comprising a bottom-closed tubular member with one end closed and the other end being open, a stopper having an upper flange portion and a lower annular skirt portion extending from the upper flange portion, the skirt portion of said stopper being fitted in the open end of said tubular member, and a cap member placed on said tubular member to increase the degree of coupling between said tubular member and stopper fitted therein, characterized in that said tubular member is provided at the circumference of its open end with an annular flange so designed that its diameter increases in the direction toward the closed bottom to form a groove between the flange of said tubular member and the flange of said stopper, and that said cap member has a bore formed in its closed end for insertion of needles and is provided with at least two projections on its inside wall at different levels, one of said at least two projections being engaged with the flange of said tubular member, the other projection being engaged with the flange of said stopper and held in a groove formed between the flange of said tubular member and that of said stopper.

In a preferred embodiment, the cap member has upper and lower projections in the form of a half-ring. These upper and lower projections are arranged in an opposite relation.

In another preferred embodiment, the cap member is provided with two kinds of projections extending inwardly from its inside wall, one projection being formed in the form of a ring, the other projections being formed in the form of a segment of a ring and axially spaced from the former.

In still another preferred embodiment, the cap member is provided with at least three pairs of upper projections with a triangular cross section and at least three lower projections with a triangular cross section, said at least three pairs of upper projections being spaced equally around the inner circumference of said cap member, said upper projections in each pair being spaced from each other, each of said lower projections being arranged below a space formed between said two projections in each pair.

The cap member may be further provided with an outwardly extending projection on a circumferential part of its closed end, said projection being positioned on the side of the projection. Preferably, the outwardly extending projection is in the form of a half-ring.

Generally, the stopper is provided at its flange portion with an upper recess and at its annular skirt portion with a lower recess to define a diaphragm portion for insertion of hollow needles between them. The diaphragm portion is designed so as to have a thickness of 0.5 to 2.5 mm. The skirt portion of the stopper is designed so as to have a length of 2 to 5 mm.

The tubular member employed in the present invention may be made of glass or a synthetic resin. Preferred synthetic resins are mixtures composed of xylylene-containing polyamide and polyethylene terephthalate and containing one or more transition metal salts.

The xylylene-containing polyamide may be produced by polymerization of at least one dicarboxylic acid and at least one xylylenediamine. The dicarboxylic acid includes, without being limited to, those such as adipic acid, pimelic acid, stearic acid, azelaic acid and sebacic acid. The above xylylenediamine includes, without being limited to, m-xylylenediamine, a mixture of m-xylylenediamine and p-xylylenediamine, a mixture of m-xylylenediamine and hexamethylenediamine. Typical transition metal salts includes, without being limited to, cobalt stearate, cobalt acetate, cobalt naphthalate, nickel acetylacetate, nickel chloride, rhodium chloride.

When the bottom-closed tubular members are to be made by a mixture of xylylene-containing polyamide and polyethylene terephthalate containing one or more transition metal salts, it is preferred to incorporate blue or violet dye or organic pigments into pellets of the mixture to improve the transparency of the tubular members. Typical dyes or pigments include blue No. 1 (C.I. 42090), blue No. 2 (C.I. 73015), blue No. 201 (C.I. 73000), blue No. 202 (C.I. 42052), blue No. 203 (C.I. 42052), blue No. 204 (C.I. 16982), blue No. 403 and violet No. 201 (C.I. 60725).

The stopper may be made of butyl rubber, natural rubber or a mixture thereof and can be produced by compression molding with a suitable rubber material.

BRIEF DESCRIPTION OF THE DRAWINGS

The invention will be explained in detail, making reference to the accompanying drawings, in which.

DETAILED DESCRIPTION OF PREFERRED EMBODIMENTS

Figure 1:
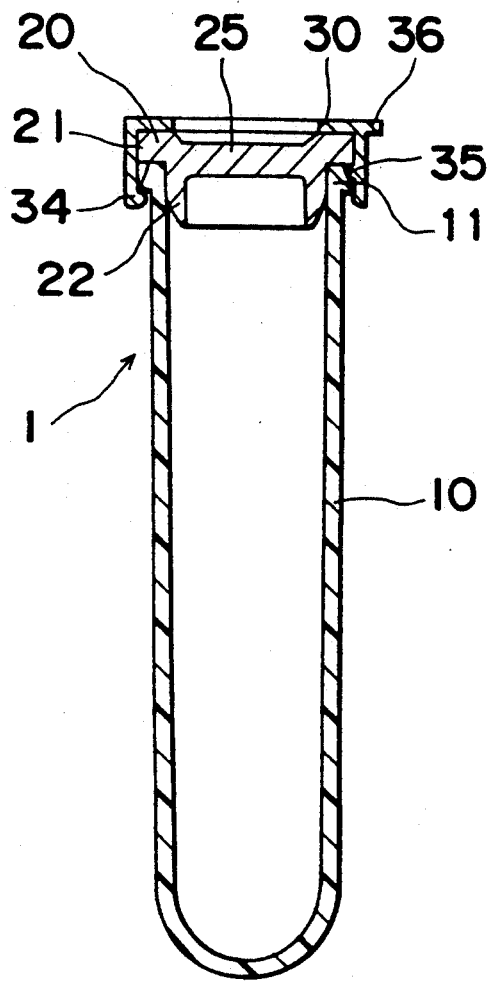
FIG. 1 is a cross-section of a blood collecting tube according to the present invention.

Referring now to FIG. 1, there is shown a blood collecting tube 1 embodying the present invention, which comprises a tubular member 10 closed at one end (or a bottom) and open at the other end (or a top), an elastomeric stopper 20 fitted in the open end of the tubular member, and a cap member 30 fitted on the top of tubular member 10.

The bottom-closed tubular member 10 is provided at its top with an outwardly extending annular flange 11 which is downwardly spread out like an unfolded fan. Such a bottom-closed tubular member can be produced with ease by injection molding, using a synthetic resin.

Figure 2:
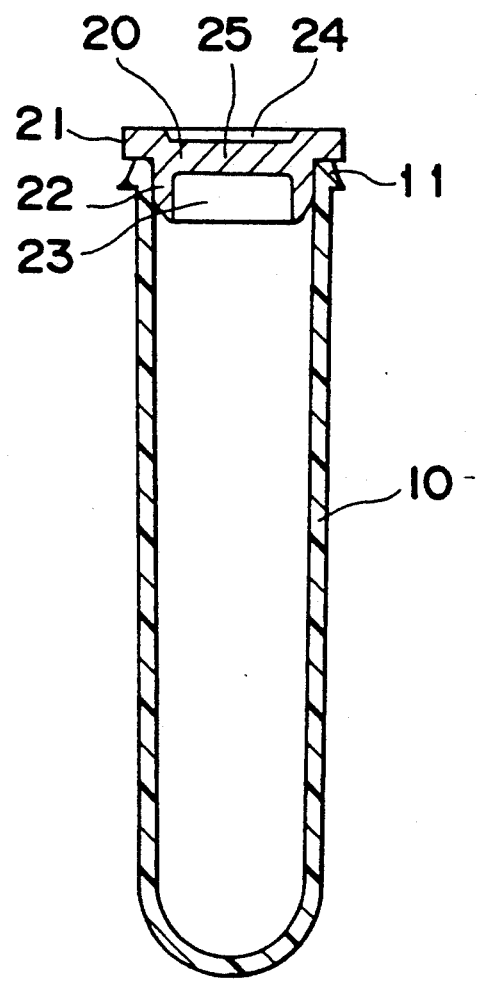
FIG. 2 is a cross-section of a bottom-closed tubular member of FIG. 1 with a stopper fitted in an open end thereof.

As illustrated in FIG. 2, the stopper 20 has a peripheral flange 21 overlying the open end of the tubular member 10, and an annular skirt portion 22 fitted in the opening of the tubular member 10 to form a sealing between stopper 20 and tubular member 10. The skirt portion 22 is so designed as to have a length of 2.5 to 5.0 mm. The stopper 20 has a cylindrical recess 23 in the central part of its skirt portion and an upper recess 24 in the central part of the flange 21. Both recesses 23 and 24 define a thickness of a diaphragm portion 25 formed between them. The diaphragm portion is so designed as to have a thickness of 0.5 to 2.5 mm to allow easy insertion and removal of a hollow needle used for blood collection or of a blood sample collection needle used in an automatic blood analyzer.

Figure 3:
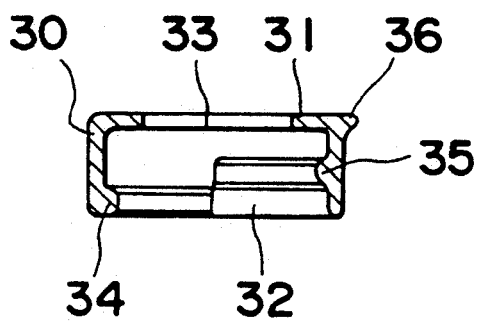
FIG. 3 is a cross-section of a cap fitted on the top of the tubular member of FIG. 1.

The cap member 30, as illustrated in FIG. 3, has a closed end 31 and an open end 32. The closed end 31 is provided at its central portion with a bore 33 for insertion and removal of a hollow needle or cannula for blood collection or a blood sample collection needle used in an automatic blood analyzer. The cap member 30 is provided with two half-ring projections 34 and 35 each of which extends inwardly from the inner peripheral surface of the cap member 30 and terminates at or around the outer surface of the tubular member 10. The projections 34 and 35 are so designed that they are in a diametrical relation and arranged at different levels so that the lower projection 34 is engaged with the lower end of the flange 11 of tubular member 10, while the upper projection 35 is engaged at its upper surface with the lower surface of the flange 21 of stopper 20 and held between the groove formed between the flange 11 of tubular member 10 and the flange 21 of stopper 20. The cap member 30 is also provided with a segmental flange 36 extending outwardly from the head portion of the cap member, indicating the direction for removal of the cap member from the tubular member and serving as a pushing portion. A difference between an inside diameter of the semicircular projection 34 or 35 and inside diameter of the opening of the cap member 30 is about 1 mm. Such a cap member may be produced with ease by injection molding, using multipurpose plastics such as polyethylene, polypropylene and the like.

When assembling the blood collecting tube of the present invention, the bottom-closed tubular member 10 is firstly evacuated to a suitable vacuum in a vacuum vessel, sealed by fitting the stopper 20 into the opening of the tubular member 10. Then, the cap member 30 is fitted on the open end of the tubular member 10. The cap member may be fitted to the tubular member 10 simultaneously with fitting of the stopper 20. This process may be carried out by a conventionally known manufacturing line for an evacuated blood collecting tube of glass.

The stopper can be removed from the opening of the tubular member along with the cap member by pushing upwardly projection 35 of the cap member as the annular flange 21 of the stopper is held between the head portion and the projection 35 of the cap member. Thus, the stopper 20 can be removed together with the cap member by one hand with ease. Also, it is possible to use the stopper 20 held in the cap member 30 to reseal the open end of the tubular member. In this case, the projection 34 of the cap member engages the flange 11 of the tubular member 10, thus making it possible to prevent the stopper from experiencing the hopping-up phenomenon.

In the blood collecting tube of the present invention, the inward projections of the cap member are engaged with the flange of the tubular member and the flanged stopper is held in place by means of the cap member and the tubular member, thus making it possible to prevent the stopper from slipping out of place when removing a hollow needle pierced in the stopper.

Further, the combination of the cap member and the flanged tubular member makes it possible to use a stopper with a shortened annular skirt portion and a thin diaphragm portion with a thickness of 0.5 to 2.5 mm. The thinner the thickness of the diaphragm of the stopper, the smaller the resistance to insertion and removal of the needle, thus making it possible to use a hollow needle with a small diameter. This makes it possible to reduce the pain to a patient caused by insertion of the piercing hollow needle.

According to the present invention, it is possible to prevent the blood collecting tube from lowering of the degree of vacuum during storage by use of a bottom-closed tubular member made of a mixture of xylylene-containing polyamide and polyethylene terephthalate and containing one or more transition metal salts.

As mentioned above, since the stopper has a low resistance to insertion and removal of a piercing needle, it is possible to apply the blood collecting tube to blood examination with an automatic analyzer of the kind wherein a hollow needle of the analyzer is directly pierced in the stopper of the blood collecting tube to introduce blood to be examined into the analyzer.

In addition, according to the present invention, decrease in the degree of vacuum of the blood collecting tube may be minimized by use of glass as a material for the tubular member, during storage for a long period of time. If the material for tubular member is not glass, it is preferred to use a mixture composed of poly-m-xylylene adipamide and polyethylene terephthalate and containing one or more organic acid salts of transition metals to prevent the evacuated blood collecting tube from a decrease of the degree of vacuum during storage.

Figure 4:
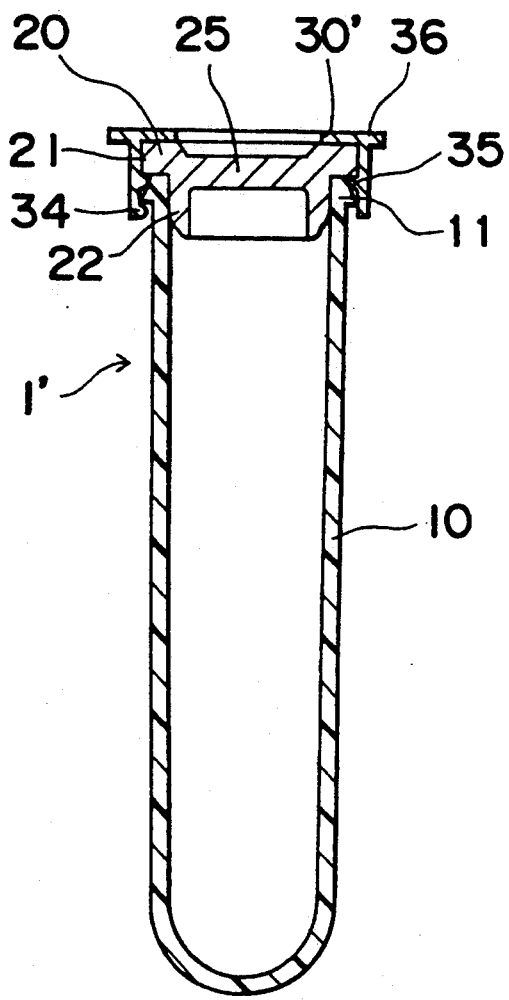
FIG. 4 is a cross-section of a blood collecting tube showing another embodiment of the present invention.

Referring now to FIG. 4, there is shown another embodiment of the blood collecting tube according to the present invention. The blood collecting tube 1' comprises a bottom-closed tubular member 10, a elastomeric stopper 20 fitted in the open end of the tubular member, and a cap member 30' fitted on the top of tubular member 10. Bottom-closed tubular member 10 has the same structure as that of bottom-closed tubular member 10 shown in FIG. 1. Also, elastomeric stopper 20 has the same structure as that of elastomeric stopper 20 of FIG. 1.

Figure 5:
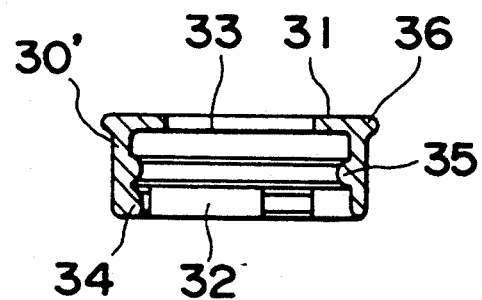
FIG. 5 is a cross-section of a cap member used in the blood collecting tube of FIG. 4.

As illustrated in FIG. 5, cap member 30' has closed end 31 and open end 32. The closed end 31 is provided at its central portion with bore 33 for insertion and removal of a hollow needle for blood collection or a blood sample collection needle used in an automatic blood analyzer. Cap member 30' is provided on its inside wall with three arched projections 34 spaced equally round the inner circumference of cap member 30', and annular projection 35 spaced upwardly from projections 34. Arched projections 34 and annular projection 35 are so designed that they have an inner diameter smaller by about 1 mm than that of cap member 30'.

When sealing the open end of bottom-closed tubular member 10, stopper 20 is first fitted in the open end of tubular member 10 and cap member 30' is fitted on bottom-closed tubular member 10. When cap member 30' is fitted in place, its lower projections 34 are engaged with annular flange 11 of tubular member 10, while upper annular projection 35 is engaged at its upper surface with the lower surface of flange 21 of stopper 20 and held between the groove formed between flanges 11 and 21 of tubular member 10 and stopper 20. At the same time, annular flange 21 of stopper 20 is urged to the end surface of tubular member 10 by cap member 30' and housed in a space formed between the lower surface of head portion 31 and the upper surface of annular projection 35 of cap member 30'.

Since lower projections 34 of cap member 30' are engaged with the annular flange 11 of tubular member 10, and since the flange of stopper 20 is forced to the end surface of tubular member 10 by cap member 30', it is possible to increase engagement between bottom-closed tubular member 10 and stopper 20. When stopper 20 is so designed as to have an annular skirt portion 22 with a length of 2 to 5 mm, it is possible remove the stopper together with cap member 30' from the tubular member by diagonally pushing up the cap member in any direction. The thus removed cap member having the stopper can be re-used to seal the bottom-closed tubular member. In this case, air contained in the tubular member is slightly compressed by the insertion of the stopper, but there is no fear that the stopper is hopped up by the action of compressed air as the lower projections of the cap member are engaged with the annular flange of the tubular member. Also, the shortened skirt portion contributes to reduce the manufacturing cost of stoppers.

In the foregoing embodiment, projection 35 is provided around the inner surface of the cap member and located above arched projections 34, but it may be located below arched projections 34. Also, projection 35 may be divided into two or more arched projections spaced equally round the inner circumference of cap member 30'.

Figure 6:
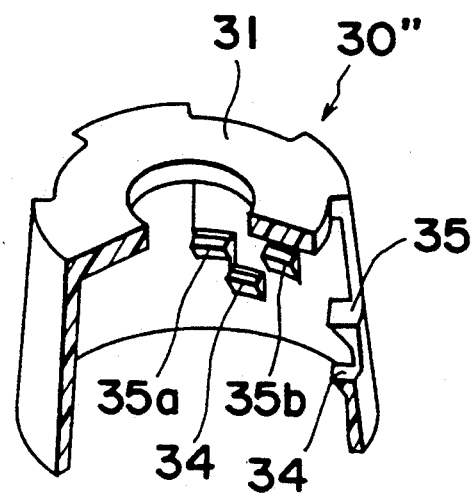
FIG. 6 is a partially cut-away perspective view of a cap member showing another embodiment of the present invention.

FIG. 6 shows another form of a cap member used to increase the fit between the stopper and the bottom-closed tubular member. This cap member 30" is provided with four pairs of upper projections with a triangular cross section and four lower projections with a triangular cross section. The four pairs of upper projections 35 are spaced equally around the circumference of the inside wall of the cap member. The upper two projections 35a, 35b in each pair are spaced from each other by a distance corresponding to a width of the lower projection 34. Each lower projection 34 is formed below a space formed between two upper projections in each pair.

Example 1

Using butyl rubber, there were prepared several kinds of stoppers having a structure shown in FIG. 1 by compression molding, each stopper having a diaphragm portion with a thickness of 1.0, 1.5 2.0 or 6.0 mm. The stopper having a diaphragm portion with a thickness of 6.0 mm is out of the scope of the present invention.

For each kind of stopper, resistance to insertion and removal of a piercing needle (size: 21 G1 ½) were measured using an autographing tester manufactured by Shimazu MFG. Co. Ltd. The measurements were carried out by piercing the needle into the diaphragm portion of the stopper at a rate of 100 mm/min and then drawing the needle therefrom at a rate of 500 mm/min. Results are shown in

TABLE 1

| In the table, values are the average of 15 measurements. | | | |
|---|---|---|---|
| Stopper No. | Thickness of diaphragm (mm) | Piercing Resistance (gf) | Drawing Resistance (gf) |
| 1 | 1.0 | 150 | 90 |
| 2 | 1.5 | 200 | 100 |
| 3 | 2.0 | 270 | 120 |
| 4 | 6.0 | 1050 | 790 |

From the results shown in Table 1, it can be seen that the piercing resistance can be considerably decreased by reducing the thickness of the diaphragm of the stopper to a thickness of not more than 2.5 mm.

Example 2

Cobalt stearate is added to a mixture composed of 100 parts by weight of polyethylene terephthalate, 1 part by weight of poly-m-xylylene adipamide and 2 parts by weight of a master pellet containing 1% of a dye (anthraquinon derivative) so that the resultant mixture contains 4 ppm of cobalt. Using the resultant mixture, there were prepared bottom-closed tubular members of FIG. 2 with a maximum capacity of 5 ml (hereinafter referred to as a "tube A") by injection molding. The bottom-closed tubular members were evacuated so as to have an initial blood collecting capacity of 2 ml or 5 ml and then sealed in vacuum by fitting the stopper prepared in Example 1 in the open end of the tubular member to prepare evacuated tubes for measurement of the vacuum retaining property. The stopper used in the example has a diaphragm portion with a thickness of 1.0 or 2.0 mm. Comparative Example 1

Using polyethylene terephthalate as a raw material, there were prepared bottom-closed tubular members (hereinafter referred to as a "tube B".) Each tube B was evacuated so as to have an initial blood collecting capacity of 2 ml or 5 ml and then sealed in vacuum by fitting the stopper prepared in Example 1 in the open end of the tubular member. The stoppers used in this comparative example have the diaphragm portion with a thickness of 6 mm.

For each kind of evacuated tube prepared in Example 2 and comparative Example 1, ten tubes were subjected to measurement of an amount of water absorbed in the tube just after their production to determine a mean value (A) of the initial blood collecting ability. Also, another ten tubes of each kind were put in storage for 1 year and then subjected to measurement of an amount of water absorbed in the tube after storage to determine a mean value (B) of the blood collecting ability after storage. The vacuum retaining rate was determined as a ratio of B/A. Results are shown in Table 2. In this table, asterisked specimens are those out of the scope of the present invention.

TABLE 2

| No. | Evacuated tube | | Rated Initial blood collecting ability | B/A (%) |
|---|---|---|---|---|
| | Vessel | Stopper | | |
| 1 | A | No. 1 | 2 ml | 106.8 |
| 2 | A | No. 1 | 5 ml | 94.0 |
| 3 | A | No. 3 | 2 ml | 107.5 |
| 4 | A | No. 3 | 5 ml | 94.2 |
| 5* | A | No. 4 | 2 ml | 108.2 |
| 6* | A | No. 4 | 5 ml | 95.4 |
| 7* | B | No. 4 | 2 ml | 95.6 |
| 8* | B | No. 4 | 5 ml | 90.2 |

From the data for specimen No. 1 through 6 in Table 2, the evacuated tubes are improved in the vacuum retaining property by use of a mixture including polyethylene terephthalate, poly-m-xylylene adipamide and containing cobalt as a material for bottom-closed tubular members, as compared with those made of polyethylene terephthalate.

Example 3

Using butyl rubber, there were prepared stoppers of FIG. 4 having a diaphragm portion with a thickness of 2.0 mm or 6 mm and an annular skirt portion with a length of 3, 5 or 10 mm.

To a mixture composed of 100 parts by weight of polyethylene terephthalate, 1 part by weight of poly-m-xylylene adipamide and 2 parts by weight of a master pellet containing 1% of anthraquinon dye, cobalt stearate was added so as to contain 4 ppm or 8 ppm of cobalt. Using the resultant mixture, there were prepared bottom-closed tubular members of FIG. 4 with a maximum capacity of 5 ml by injection molding.

Using polyethylene terephthalate as a material, bottom-closed tubular members with no flange were prepared in the same manner as above.

Using polypropylene, cap members of FIG. 5 were prepared by injection molding.

The bottom-closed tubular members were evacuated so as to have an initial blood collecting capacity of 2 ml or 5 ml and then sealed in vacuum by fitting the stopper in the open end of each tubular member. The cap member was then fitted on each evacuated tubular member to prepare the evacuated blood collecting tubes listed in Table 3.

TABLE 3

| No. | Stopper Thickness of diaphragm (mm) | Length of Skirt (m) | Cobalt content (ppm) | cap |
|---|---|---|---|---|
| 9 | 2.0 | 3 | 4 | with cap |
| 10 | 2.0 | 3 | 8 | with cap |
| 11 | 2.0 | 5 | 4 | with cap |
| 12 | 2.0 | 5 | 8 | with cap |
| 13* | 6 | 10 | none | no cap |

For ten evacuated blood collecting tubes of each kind, measurements were made on an amount of water absorbed by the tube just after its production in the same manner as that of blood collection to determine an average (A) of the initial blood collecting ability (A). Also, another ten tubes of each kind were put in storage for 1 year at room temperature, and then subjected to measurement of an amount of water absorbed by the tube after storage to determined an average (B) of the blood collecting ability after storage. The vacuum retaining rate was determined as a percentage of B/A. Results are shown in Table 4. In this table, asterisked specimens are those out of the scope of the present invention.

TABLE 4

| No. | Rated Initial blood collecting ability | |
|---|---|---|
| | 2 mm | 5 ml |
| 9 | B/A = 102.5 | B/A = 93.2 |
| 10 | B/A = 105.8 | B/A = 94.4 |
| 11 | B/A = 106.6 | B/A = 94.2 |
| 12 | B/A = 110.2 | B/A = 95.0 |
| 13* | B/A = 95.6 | B/A = 90.2 |

What is claimed is:

1. A blood collecting tube comprising:
   a closed-bottom tubular member with one end closed and the other end being open;
   a stopper having an upper flange portion and a lower annular skirt portion extending from the upper flange portion, the skirt portion of said stopper being fitted in the open end of said tubular member; and
   a cap member placed on said tubular member to increase friction between said tubular member and stopper fitted therein,
   wherein said tubular member is provided at a circumference of its open end with an annular flange having its diameter increase in a direction toward the closed bottom to form a groove between the annular flange of said tubular member and the upper flange portion of said stopper, and wherein said cap member has a bore formed in its closed end for insertion of needles and is provided with at least two projections on an inside wall thereof at different levels, one of said at least two projections being engaged with the annular flange of said tubular member, the other projection being engaged with the upper flange portion of said stopper and held in a groove formed between the annular flange of said tubular member and the peripheral flange of said stopper.

2. The blood collecting tube according to claim 1, wherein said cap member has upper and lower inner projections in the form of a half-ring, said upper and lower projections being arranged on opposing sides of an inner peripheral wall of said cap member.

3. The blood collecting tube according to claim 1, wherein said cap member is provided with two projections extending inwardly from its inside wall, one projection being formed in the form of a ring, the other being formed in the form of a segment of a ring and axially spaced from the former.

4. The blood collecting tube according to claim 1, wherein said cap member is provided with at least three pairs of upper projections with a triangular cross section and at least three lower projections with a triangular cross section, said at least three pairs of upper projections being spaced equally around the inner circumference of said cap member, said upper projections in each pair being spaced from each other, each of said lower projections being arranged below a space formed between said two projections in each pair.

5. The blood collecting tube according to claim 1, wherein said cap member is further provided with an outwardly extending projection on an outer circumference of its closed end, said outwardly extending projection being positioned on the side of the upper projections.

6. The blood collecting tube according to claim 5, wherein said outwardly extending projection is in the form of a half-ring flange.

7. The blood collecting tube according to claim 1, wherein said stopper is provided at its flange portion with an upper recess and at its annular skirt portion with a lower recess to define a diaphragm portion for insertion of hollow needles therebetween, said diaphragm portion having a thickness of from 0.5 to 2.5 mm.

8. The blood collecting tube according to claim 1, wherein said stopper has a skirt portion with a length of from 2 to 5 mm.

9. The blood collecting tube according to claim 2, wherein said closed-bottom tubular member is made of resin produced from a mixture of xylylene-containing polyamide, polyethylene terephthalate and one or more transition metal salts, wherein said stopper is made of an elastomeric material selected from the group consisting butyl rubbers, natural rubber and mixtures thereof.

10. The blood collecting tube according to claim 9, wherein said xylylene-containing polyamide is a polymer produced from at least one dicarboxylic acid and at least one xylylenediamine.

11. The blood collecting tube according to claim 1, wherein said closed bottom tubular member is maintained at a pressure lower than atmospheric pressure.

* * * * *